United States Patent [19]
Noeth et al.

[11] Patent Number: 5,538,870
[45] Date of Patent: Jul. 23, 1996

[54] METHOD FOR PREPARING NUCLEIC ACIDS FOR ANALYSIS AND KITS USEFUL THEREFOR

[75] Inventors: Lisa S. Noeth, Fishers; Mary Dasovich-Moody, Indianapolis; Melissa R. Winget, Zimsville, all of Ind.

[73] Assignee: Boehringer Mannheim Corporation, Indianapolis, Ind.

[21] Appl. No.: 309,575

[22] Filed: Sep. 21, 1994

[51] Int. Cl.$^6$ ............... C17Q 1/68; C17P 1/34; C07H 21/02; C17N 15/00
[52] U.S. Cl. ............ 435/91.2; 435/6; 435/91.1; 435/270; 435/183; 536/23.1; 536/74.33; 536/75.3; 935/76; 935/77; 935/78
[58] Field of Search ............... 435/6, 91.1, 91.2, 435/270, 183; 935/1, 77, 78, 76; 536/23.1, 24.33, 25.3; 252/89

[56] References Cited

U.S. PATENT DOCUMENTS

| | | | |
|---|---|---|---|
| 4,683,202 | 7/1987 | Mullis | 435/91 |
| 4,908,318 | 3/1990 | Lerner | 435/270 |
| 5,010,183 | 4/1991 | Macfarlane | 536/27 |
| 5,128,247 | 7/1992 | Koller | 435/91 |
| 5,130,423 | 7/1992 | Van Ness et al. | 536/27 |
| 5,231,015 | 7/1993 | Cummins et al. | 435/91 |
| 5,284,940 | 2/1994 | Lin et al. | 536/25.4 |
| 5,294,681 | 3/1994 | Krupey | 525/327.6 |
| 5,376,527 | 12/1994 | Robson et al. | 435/6 |

FOREIGN PATENT DOCUMENTS

| | | |
|---|---|---|
| 0442026 | 8/1991 | European Pat. Off. |
| 0574267 | 12/1993 | European Pat. Off. |
| WO89/07603 | 8/1989 | WIPO |
| WO92/12253 | 7/1992 | WIPO |

OTHER PUBLICATIONS

Jones et al., "A Rapid Method for Purication of Target DNA from Complex Biological And Environment Samples For Polymerase Chain Reaction (PCR) DNA Amplification" Abtract p–10, 93rd General Meeting of the American Society For Microbiology, May 16–20.

Haselbeck et al., "Studies on the effect of the incubation conditions, various detergents and protein concentration on the enzymatic activity of N–glycosidase R (Glycopeptidase F), and Endoglycosidase F", Topics In Biochemistry 8: 1–4 (1988).

Ehrlich et al., PCR Technology: Principles and Applications for DNA Amplification, pp. 19–21.

Boehringer Mannheim Biochemicals Catalogue: Detergents For Membrane Research.

Casareale et al., "Improved Blood Sample Processing for PCR" in PCR Methods and Applications (Cold Spring Harbor Laboratories, N.Y. 1992, pp. 149–153).

Gibson et al., "A Simple And Rapid Method For Detecting Human Immunodefiency Virus By PCR", J. Virol. Meth. 32: 286 (1991).

Blin et al., "A General Method For Isolation of High Molecular Weight DNA from Eukaryotes", Nucl. Acid Res. 3(9): 2303–2308 (1976).

*Primary Examiner*—W. Gary Jones
*Assistant Examiner*—Bradley L. Sisson
*Attorney, Agent, or Firm*—Felfe & Lynch

[57] ABSTRACT

Methods useful in purifying nucleic acids from whole cell samples are described. This is accomplished by adding one or both of a non-phenyl group containing non-ionic detergent or a cross-linked, polycarboxylic acid. Kits which can be used in the methods are also described.

7 Claims, 3 Drawing Sheets

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GTACGGCTGT CATCACTTAG ACCTCA                                    26
```

( 2 ) INFORMATION FOR SEQ ID NO: 2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
AGCACACAGA CCAGCACGTT                                           20
```

METHOD FOR PREPARING NUCLEIC ACIDS FOR ANALYSIS AND KITS USEFUL THEREFOR

FIELD OF THE INVENTION

This invention relates to the purification of nucleic acid molecules. More particularly, it relates to the preparation of nucleic acid molecules for subsequent use in analytical methodologies, especially amplification assays.

BACKGROUND AND PRIOR ART

The determination of particular nucleic acid molecules, or expression of these molecules, is an extremely important facet of analytical and clinical chemistry. A vast number of different nucleic acid assays are known in the field. All of these assays may be said to have a common goal, i.e., the identification of particular nucleic acid molecules in samples. Achievement of this aim permits one to identify infections, such as bacterial or viral infections, to type tissues, to identify individuals (so-called "DNA fingerprinting"), and so forth.

One of the problems in nucleic acid assays is that the target materials, i.e., a particular nucleic acid molecule, exists as only one or very few copies. Thus, there has been a great deal of interest in purifying nucleic acid molecules so that the chances of actually finding the desired molecule is maximized.

Classic techniques have been developed for purifying nucleic acid molecules. One of the most basic of these is the method described by Maniatis et al., in *Molecular Cloning: A Laboratory Manual* (New York, Cold Spring Harbor Laboratory, 1982, pp. 280-1). This method teaches the lysis of target cells, using proteases, followed by phenol/chloroform extraction. The method takes a very long time to complete, and involves the use of hazardous, carcinogenic substances. Some of the problems associated with this method are discussed in Miller et al., WO89/07603 (Aug. 24, 1989), incorporated by reference. Further, the phenol/chloroform based methodologies all require the use of an alcohol precipitating agent, such as ethanol or isopropanol to separate nucleic acid molecules from their solvent. Risk of damage to the desired material, as well as loss of it, is very great.

The need for continued improvement in this very basic technology can be seen via the large number of patents and non-patent publications directed to it. These references are directed to improvements in obtaining desired nucleic acid molecules. They evidence the many different approaches one may take.

U.S. Pat. No. 5,231,015 to Cummins, e.g., teaches the use of a metal ion in lysis solutions. The ion is a cofactor for naturally occurring nucleic acid molecule polymerases. The theory is that the metal ions improves the inherent ability of native polymerases to copy the nucleic acid molecule of interest. Such a technique is especially useful in amplification methodologies, elaborated infra. U.S. Pat. No. 5,130,423, to van Ness et al., alleges improvements in the use of phenyl derivatives, such as benzyl alcohol, in the extraction of DNA. U.S. Pat. No. 5,128,247 to Koller is along the same lines, and teaches the use of chaotropic agents to lyse cells, followed by treatment with sulfated polysaccharide proteins, such as heparin.

U.S. Pat. No. 5,010,183 to Macfarlane, advises the art to use cationic detergents to purify nucleic acids, while U.S. Pat. No. 4,908,318, teaches detergent based lysis followed by solubilizing the nucleic acid molecules, and then spooling these.

U.S. Pat. No. 5,284,940 to Lin, et al. suggests the use of transferrin, globin, or serum albumin to prevent the action of polymerase inhibitors during an amplification reaction.

Most of the patents discussed supra deal with the preparation of samples for subsequent use in amplification assays, especially the very well known polymerase chain reaction, or "PCR" technique. This methodology, described in Mullis et al., U.S. Pat. No. 4,683,202, and incorporated by reference herein, shows how one can obtain multiple copies of a desired nucleic acid molecule via the use of one or two nucleic acid molecule primers, together with a polymerase, such as *Thermus aquaticus,* or "Taq" polymerase. The procedure by which the amplified nucleic acid molecules are obtained, however, is essentially that of Maniatis et al. The desire to improve this methodology can be seen, e.g., in Casareale et al., "Improved Blood Sample Processing For PCR" in *PCR Methods and Applications* (Cold Spring Harbor Laboratories, New York, 1992, pp. 149–153), incorporated by reference. The paper discusses the inherent limitations on PCR, including small sample volume, inhibition of application, sample stability, and so forth. Casareale et al. report improvements in the isolation of nucleic acids by using heat and detergents. The detergent used was Nonidet P-40, the chemical name of which is ethyl phenol poly(ethylene glycolether)$_n$, where "n" is usually a whole number of about 11. The success is attributed to a reduction in inhibition of DNA amplification. Others have made similar assertions, for example, in Ehrlich et al., ed. *PCR Technology: Principles & Applications for DNA Amplification* pp. 19–21, the use of Nonidet P-40, in combination with Tween 20 (Poly(oxyethylene)$_n$-sorbitane-monolaurate, when "n" is usually 20) is said to prevent inhibition of Taq polymerase in lysed samples where sodium dodecyl sulfate (SDS) was used in the lysing agent. The effect of the SDS is to inhibit any polymerases used in the amplification process. The detergent combination is alleged to alleviate the problem, when DNA and $Mg^{2+}$ (a cofactor for Taq polymerase) are present, at 37° C.

The use of detergents to neutralize SDS is, in a theoretical sense, not surprising. Haselbeck et al, "Studies on the effect of the Incubation Conditions, Various Detergents and Protein Concentration on the Enzymatic Activity of N-Glycosidase F (Glycopeptidase F), and Endoglycosidase F", in Topics In Biochemistry 8: 1–4 (1988), discuss the general inhibitory effect of SDS on enzymes. Haselbeck et al., then show that either NP-40 or Triton X-100 (octylphenolpoly-(ethylene glycol ether)$_n$ where "n" is about 10), inhibit the effect of SDS on the listed enzymes. Generalizations are not made and, indeed, as will be discussed, infra, broad generalizations in fact cannot be made as to the effect of detergents on eliminating the impact of SDS on amplification processes.

The body of art discussed supra points to one of the problems addressed by the invention. In brief, the agents used to lyse cells, and thereby free nucleic acids for amplification, frequently include sodium dodecyl sulfate, or "SDS". SDS however, has the undesired side effect of inhibiting the polymerases necessary to carry out amplification reactions.

Another problem in the art is the need to obtain very pure nucleic acid samples in as brief an amount of time as is possible. When cells are lysed, materials other than the target nucleic acid molecules are released, and these must be deemed contaminants. In the case of whole blood samples, there is a particularly serious problem caused by the voluminous amount of protein released, relative to the amount of nucleic acids. Included in these proteins are polymerase inhibitors. Porphyrin ring containing compounds, especially heme and its derivatives, are notoriously well known as polymerase inhibitors. Clearly, it is very important to remove these materials from samples.

The alcohol precipitation approach, discussed supra, is one way of removing nucleic acid molecules from impurities. Applicants will not repeat the drawbacks of this approach again. It would be desirable if one could quickly, and efficiently obtain pure samples of nucleic acid molecules without the need for an alcohol precipitation step. It is even more desirable to have such a method available where the nucleic acid molecules thus purified could be used immediately in an amplification process.

In U.S. Pat. No. 5,294,681 to Krupey, which is incorporated by reference in its entirety, a family of water insoluble, cross-linked polyhydroxy polycarboxylic acid molecules are described. These molecules are:

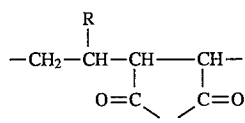

wherein one carbonyl group of at least one maleoyl moiety thereof in each strand is covalently linked to a

to provide the presence therein of at least one cross linking moiety of the formula:

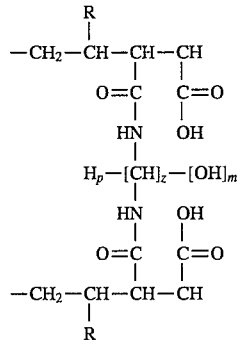

wherein R is hydrogen or lower alkylene or lower alkoxy of 1–4 carbon atoms, or phenyl, z is an integer of 1–4, p is 0 or an integer up to z–1, m is 1 or an integer up to z, wherein the ratio of cross-links to poly (alkylene carbonic acid) strands is between 1 and about 200 to 2 are described as being useful for recovering proteins from aqueous media. The molecules sequester any proteins in the sample. A product based upon this patent, known as PROCIPITATE, is commercially available. The commercial product does not, however, adumbrate the particular acids used therein, but only refers to the patent.

Krupey describes the use of his novel molecules in the separation of DNA from proteins generally; however, the methods are only described generally, and always refer to the use of aqueous guanidium thiocyanate, a chaotrope, and the lysing agent. These methodologies are all reported in the context of methods where nucleic acid precipitation via the use of, e.g., alcohols, is also used.

Thus, there is another problem in the art in that the desirability of separating proteins is linked to the precipitation of DNA, which is not desirable.

It has now been found, first of all, that generalizations regarding detergent based inactivation of SDS cannot be made in the context of preparing samples for nucleic acid amplification. This is especially true for non-ionic detergents, where it has been found that phenyl group containing detergents, such as the "Triton" family of detergents, do not function to inhibit sodium dodecyl sulfate. Thus, one aspect of the invention is based upon the surprising recognition that non-ionic detergents which do not contain a phenyl group can be used alone, to inhibit sodium dodecyl sulfate, thus permitting improved purification of nucleic acid samples from whole cells.

A second aspect of the invention, also surprising, is that cross linked, polyhydroxy polycarboxylic acids of formula

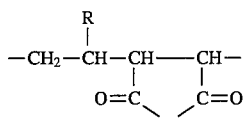

wherein one carbonyl group of at least one maleoyl moiety thereof in each strand is covalently linked to a

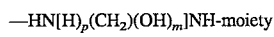

to provide the presence therein of at least one cross linking moiety of the formula:

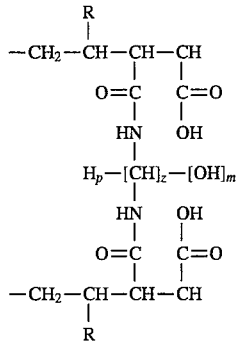

wherein R is hydrogen or lower alkylene or lower alkoxy of 1–4 carbon atoms, or phenyl, z is an integer of 1–4, p is 0 or an integer up to z–1, m is 1 or an integer up to z, wherein the ratio of cross-links to poly (alkylene carbonic acid) strands is between 1 and about 200 to 2 can be used in methods for purifying nucleic acids, where an alcohol precipitation step may be left out. Use of these compounds also inhibit SDS, and thus may be used alone or together with the detergents discussed supra.

These methods may be employed separately, or together.

These, and other aspect of the invention, will be seen in the disclosure which follows.

BRIEF DESCRIPTION OF THE FIGURES

FIG. 1A presents studies on the effect of constant pH, where salt concentrations are varied (at a pH of 6).

FIG. 1B shows results obtained when pH was held constant, but salt concentration varied (at a pH of 7).

FIG. 1C shows further results where salt concentration was held constant and pH varied.

In FIGS. 1A and 1B, the salt concentrations used were 100 mM and 150 mM, while in FIG. 1C, it was 50 mM. The pH used in FIG. 1A was 6, in FIG. 1B, 7 and in FIG. 1C, both 6 and 7.

DETAILED DESCRIPTION OF PREFERRED EMBODIMENTS

EXAMPLE 1

Figure 1A:
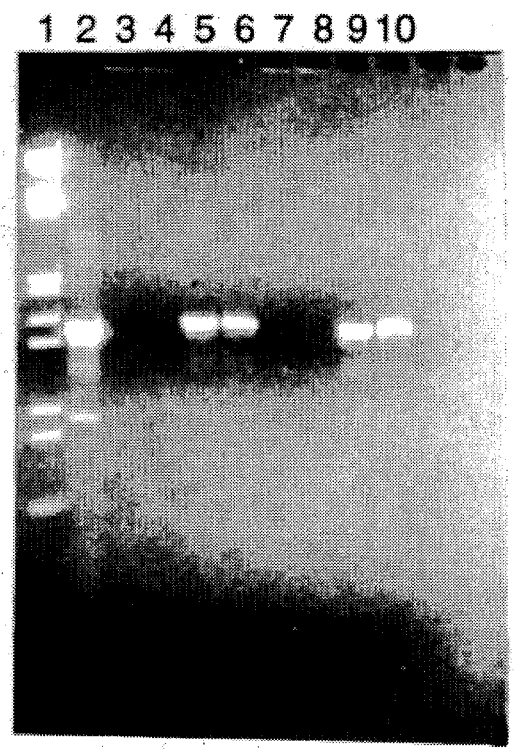
FIGS. 1A–1C show results obtained following polymerase chain reaction on a 1.5 kilobase β-globin segment from human white blood cell DNA.

This example sets forth the protocol for carrying out the polymerase chain reaction ("PCR") referenced to in examples 2 and 3 which follow.

After sample preparation, a 1.5 kilobase segment of the β-globin gene was amplified. Sample was combined with a PCR reagent, as follows:

| | |
|---|---|
| distilled water: | 70 parts |
| reaction buffer: | 10 parts |
| 25 mM MgCl$_2$: | 6 parts |
| sample DNA: | 10 parts |
| dNTPs: | 2 parts |
| primer A: | 1 part |
| primer B: | 1 part |

The sequence of primer A was: GTACGGCTGT CAT-CACTTAG ACCTCA (SEQ ID NO: 1)

The sequence of primer B was: AGCACACAGA CCAG-CACGTT (SEQ ID NO: 2)

A 0.5 μl sample of Thermus aquaticus DNA polymerase (2.5 U) was added to these reagents, as explained in the following cycling protocol.

The first cycle was as follows:

denaturing (97° C., 7 minutes)

annealing (59° C. 1 minute)

Pause, then add 0.5 μl (2.5 U) Taq DNA polymerase to each sample, maintaining a temperature of 59° C.

polymerizing (72° C., 2 minutes)

This was carried out once, followed by 30 cycles as follows:

denaturation (94° C., 1 minute)

annealing (60° C., 2.5 minutes)

polymerizing (72° C., 2 minutes)

Finally, 1 cycle to extend was carried out (72° C., 7 minutes). DNA was fractionated on 2.0% LE agarose gels, with molecular weight markers being provided on lanes which were a part of the gel, as well as with controls. The gels are provided as figures, explained within the examples which follow.

EXAMPLE 2

For this, and following experiments, the following reagents were used:

(i) red blood cell lysis buffer: 140 mM NH$_4$Cl, 17 mM Tris (pH 7.65);

(ii) white blood cell lysis buffer: one of six different alternatives: in each of the six alternatives, 10 mM Tris, and 0.1% SDS were combined. One of these different salt concentrations were used (50, 100, or 150 mM NaCl). The pH was either 6 or 7. This yields six lysis buffers, i.e.:

50 mM NaCl, 10 mM Tris, 0.1% SDS (pH 6, or pH 7);

100 mM NaCl, 10 mM Tris, 0.1% SDS (pH 6, or pH 7);

150 mM NaCl, 10 mM Tris, 0.1% SDS (pH 6 or pH 7).

In each sample run, 500 μls of whole blood were added to 1 ml of the red blood cell lysis buffer. The mixture was then incubated for 5 minutes, after which it was centrifuged, at 2500 rpms, for 5 minutes. Incubation times may vary, as desired. This yielded a pellet, and a supernatant. The supernatant was discarded, and the pellet resuspended in 1 ml of fresh red blood cell lysis buffer. The new solution was spun for 3 minutes at 2500 rpms. The resulting pellet was then suspended in one of the six white blood cell lysis buffers. The new suspension was heated at 65° C. for 5 minutes. Following heating, the sample was used in one of the alternatives which follow.

EXAMPLE 3

The suspensions prepared in example 2 were combined with 700 μl of PRO-CIPITATE. The mixture was incubated for 5 minutes, and then spun at full speed in a centrifuge for 5 minutes.

Samples were used in polymerase chain reactions, as elaborated supra in example 1. Following the amplification, amplification products were run on 2.0% LE agarose gels.

Figure 1B:
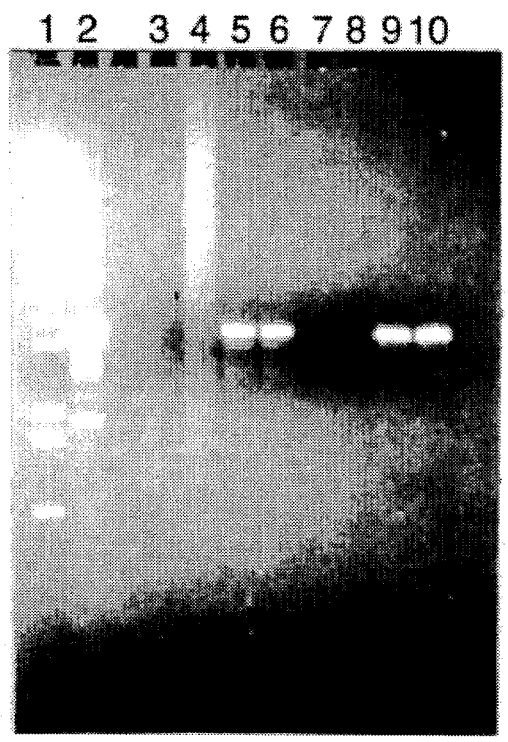
Figure 1C:
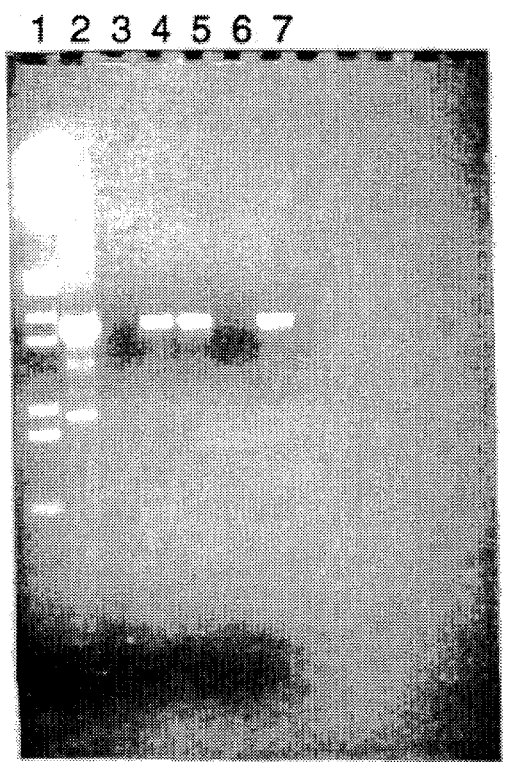

The results are presented in FIGS. 1A, 1B and 1C, attached hereto, which set forth gels of the experiments. In each case:

Lane 1 of the gel shows molecular weight markers.

Lane 2 is a control.

In FIG. 1A, lanes 3 and 4 show results when 100 mM NaCl, 10 mM Tris, and 0.1% SDS (pH 6), were used without PRO-CIPITATE, while lanes 5 and 6 show the results obtained when the buffer had the PRO-CIPITATE added. In lanes 7 and 8, the buffers were 150 mM NaCl, with 10 mM Tris and 0.1% SDS, pH 6, without PRO-CIPITATE.

In lanes 9 and 10, the higher salt buffers were used, with PROCIPITATE.

FIG. 1B parallels the results shown in FIG. 1A, but at a pH of 7.

In FIG. 1C, results are presented, paralleling 1A and 1B. In this case, however, lane 3 used 50 mM NaCl, 10 mM Tris, 0.1% SDS, at a pH of 6. Lanes 4 and 5 are identical, except that PROCIPITATE is used. Lane 6 parallels lane 3, except the pH is 7. Lane 7 parallels lanes 4 and 5 except the pH is 7.

The results presented in FIGS. 1A, 1B and 1C show that when PRO-CIPITATE was used, the signal was clearly better. This result was independent of said concentration, or of pH and thus the effect can only be attributed to the presence of PRO-CIPITATE.

EXAMPLE 4

This experiment describes the use of non-ionic detergent in combination with SDS. It shows that the former neutralized the effect of the latter, thereby permitting PCR analysis of a sample.

A 500 μl sample of whole blood was combined with 1 ml of the red blood cell lysis buffer discussed in example 3. The materials were rocked (i.e., incubated) for five minutes, and then spun for five minutes at 2500 rpm. As in example 2, supra incubation times may vary, as desired. The pellet was combined with an additional 1 ml of the red blood cell lysis buffer, resuspended and then spun for three minutes at 2500 rpm.

The resulting pellet was then combined with 500 μl of a white blood cell lysis buffer. The lysis buffer contained one of the following, in a first set of tests:

a. SDS only;
b. Triton X-100 only;
c. SDS+ Triton X-100;
d. SDS+ Tween 20;
e. Tween 20 alone.

In a second set of tests, PRO-CIPITATE was also combined with the buffers, as follows:

a. SDS (lysis buffer), then PRO-CIPITATE, then Tween 20;
b. SDS (lysis buffer), then Tween 20, then PRO-CIPITATE;
c. SDS+ Tween 20 (lysis buffer), then PRO-CIPITATE;
d. SDS (lysis buffer), then PRO-CIPITATE.

In the first set of tests, samples were combined with lysis buffer, and then heated for five minutes at 65° C., after which polymerase chain reactions were carried out in accordance with example 1. In the second set of experiments, the lysis buffer was added first (SDS alone, in "a", "b" and "d", or SDS+Tween 20 in "c"), then samples were heated as in the first set of experiments. Then the remaining reagents were added (in "a", first PRO-CIPITATE then Tween 20; in "b" first Tween 20 then PRO-CIPITATE; in "c" and "d", PRO-CIPITATE alone).

Figure 2:
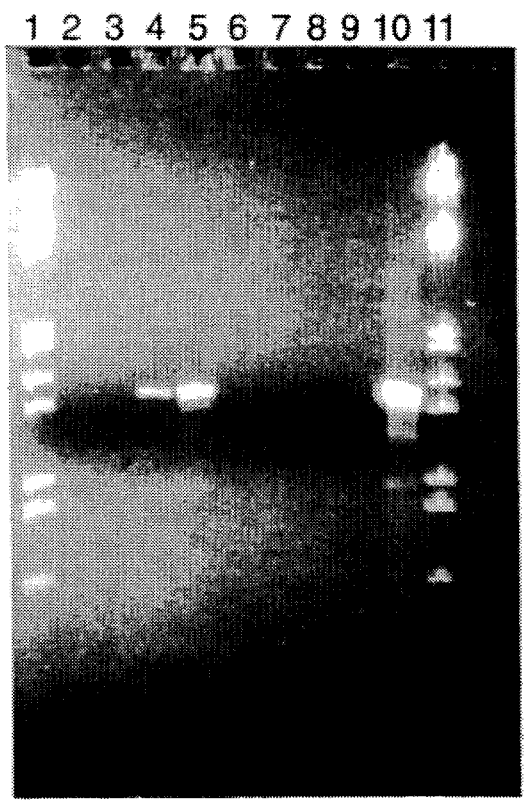
FIGS. 2–2B depict the results obtained when the phenyl group containing non-ionic detergent Triton X-100 was used to try to inhibit sodium dodecyl sulfate.
Figure 2A:
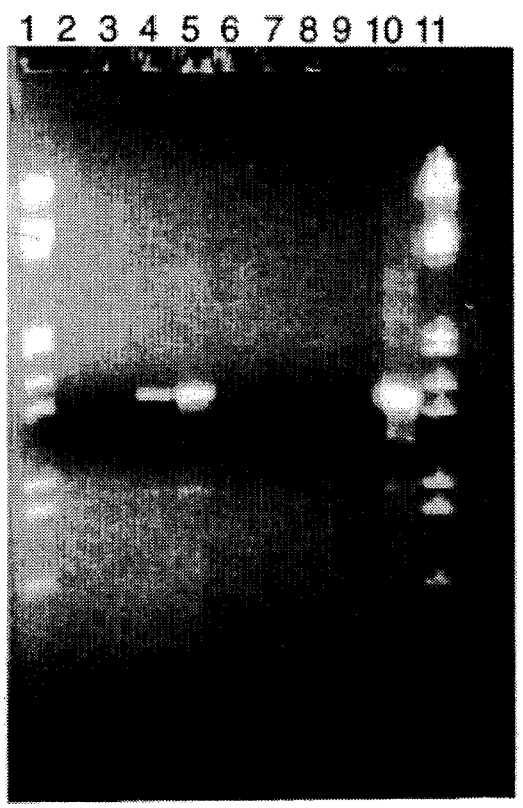
Figure 3:
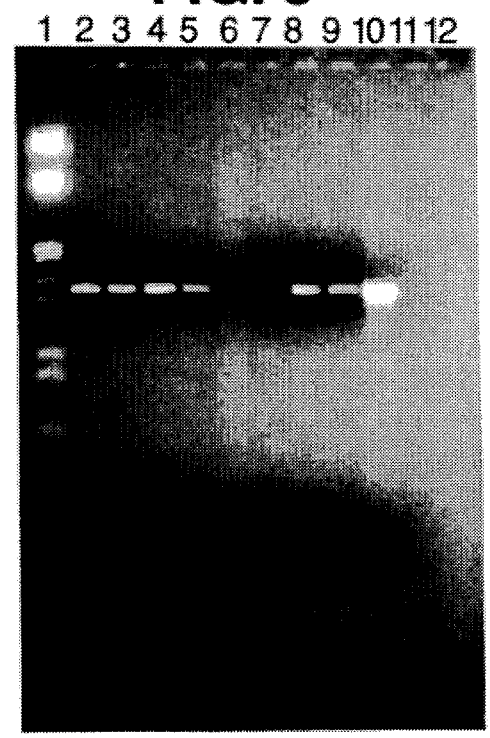
FIGS. 3–3B shows results obtained when non-phenyl group containing non-ionic detergent Tween 20 was used to inhibit sodium dodecyl sulfate.

FIGS. 2 and 3 depict the results.

In FIG. 2, lanes 1 and 11 are molecular weight markers. Lanes 2 and 3 are results secured when SDS was used alone. Lanes 4 and 5 are results from Triton X-100 alone. Lanes 6 and 7 are combinations of SDS and Triton, while lanes 8 and 9 show the sequential use of SDS and Triton X-100, rather than simultaneous use. Lane 10 is a control.

Note the banding in lanes 4 and 5, when Triton X-100 was used. There was no banding when SDS was present, however, showing that Triton X-100 failed to inactivate SDS.

Figure 2B:
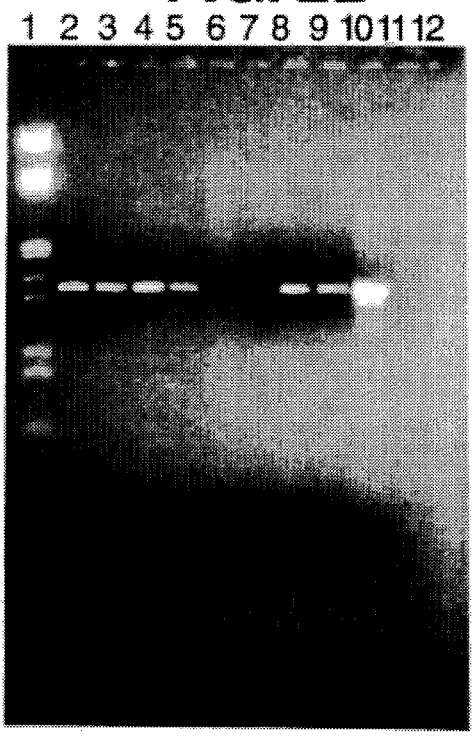

In contrast, however, the results shown in FIG. 2b prove that Tween 20 did in fact inactivate the SDS. In FIG. 2b, lane 1 shows molecular weight markers. Lanes 2 and 3 show the use of SDS+ Tween 20 (simultaneous use). Lanes 4 and 5 present results when the materials were used in sequence. Lanes 6 and 7 resulted from the use of SDS alone, and lanes 8 and 9, Tween 20 alone. Lane 10 is a control.

Figure 3B:
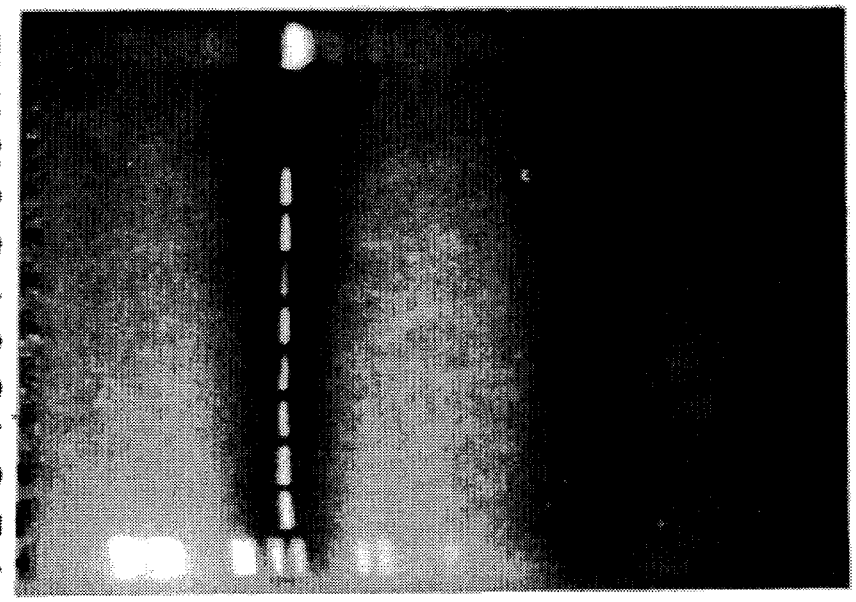
Figure 3A:
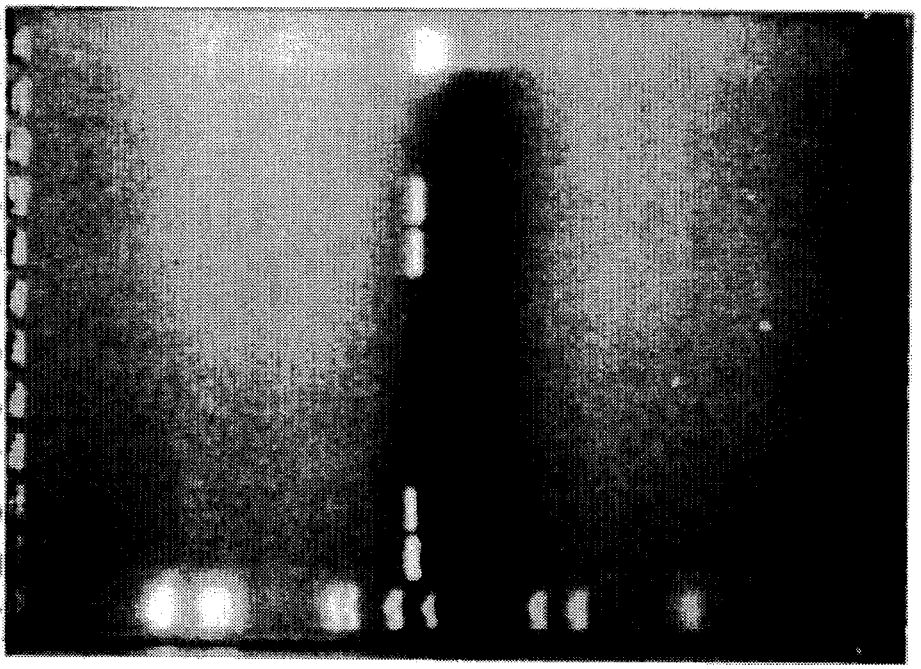

In FIGS. 3A and 3B, work with PRO-CIPITATE is shown. In FIG. 3A, lane 1 is a molecular marker, and lane 12 is a control. Lanes 2 and 3 used SDS and PRO-CIPITATE, while lanes 4 and 5 used Triton X-100 then PRO-CIPITATE. Lanes 6 and 7 used SDS combined with Triton X-100, followed by PRO-CIPITATE. In lanes 8 and 9, SDS was followed by PRO-CIPITATE, and then Triton X-100. In lanes 10 and 11, SDS was followed by Triton X-100, then PRO-CIPITATE. In FIG. 3B, lanes 1 and 12 are the same as in lane 3A. Lanes 2 and 3 show the use of SDS, then PRO-CIPITATE, then Tween 20. Lanes 4 and 5 show SDS, followed by Tween 20, and then PRO-CIPITATE. Lanes 6 and 7 used SDS with Tween 20, followed by PRO-CIPITATE, while lanes 8 and 9 show SDS followed by PRO-CIPITATE. Lanes 10 and 11 were blanks.

In each case, the PRO-CIPITATE facilitated amplification of the target sequence.

The preceeding examples describe the invention, which relates to methods for preparing nucleic acid molecules for assays, such as nucleic acid amplification. In one aspect of the invention, whole cell samples are lysed to release nucleic acid molecules contained therein. This is followed by addition of at least one water insoluble, cross linked polyhydroxy polycarboxylic acid of the formula described, supra, and in U.S. Pat. No. 5,294,681, to Krupey, the disclosure of which is incorporated by reference herein. Reagents containing such materials are available under the registered trademark PRO-CIPITATE®, but specifics of the formulations are not permitted by the product. The Krupey patent, however, has complete particulars on how to secure the polycarboxylic acids.

Following the addition of the polycarboxylic acids, the nucleic acids in the sample may be recovered directly, without the traditional step of adding an alcohol to precipitate them. As a result, one may, if desired, immediately contact the sample with reagents necessary to carry out nucleic acid amplification. Such reagents include, e.g., polymerases, such as *Thermus aquaticus* nucleotide polymerases, or other equivalent enzymes, for example PWO polymerase. The reagents may also include, e.g., suitable primers, deoxy nucleotides, buffers, and so forth, in accordance with any of the many well known protocols for nucleic acid amplification. Among the families of nucleic acid amplification assays are the now classic polymerase chain reaction or "PCR", the ligase chain reaction, or "LCR" and others, all of which will be known to the skilled artisan, and need not be listed here.

The methodologies described herein can be used to secure nucleic acids from any cell which contains them. (Note, in this context that red blood cells, e.g., do not contain nucleic acids). Preferably, eukaryotic cells, such as mammalian cells are treated, human cells being especially preferred. Of the myriad of human cells which can be so treated, it is particularly preferred to treat white blood cells, either in a purified sample, or as part of a whole blood sample.

The preparative methodology, discussed generally above, can be adapted for various cells types. It is well known, as indicated by the cited art, that different cells are preferably lysed to release their nucleic acids by different lysing agents. Thus, when a whole cell sample is being treated, it is convenient to utilize two different lysis buffers, one for red blood cells and one for white blood cells. Again, as is indicated by the cited art, the artisan is familiar with a myriad of different buffers.

It is especially preferred, when using the polycarboxylic acids, to heat the sample following lysis but before adding the polycarboxylic acid. This heating is preferably at a temperature in the range of from about 50° C. to about 70° C., for at least one minute. Preferably, the heating step extends for no more than 10 minutes.

One may also utilize a centrifugation step after adding the polycarboxylic acid to the sample, so as to further purify the nucleic acids from the sample. Again, protocols of centrifugation are well known.

Following separation of the nucleic acids in accordance with the methods of the invention outlined above, one may store the nucleic acids for later use, or immediately carry out amplification. In the latter case, amplification reagents are added directly to an aliquot of the released nucleic acids, and the reaction is allowed to proceed.

Another aspect of the invention described, e.g., by the examples in the use of detergents which (i) are non-ionic and (ii) do not contain phenyl groups, in lysis buffers which also contain sodium dodecyl sulfate, or "SDS". SDS is a standard, and almost ubiquitous material in lysis agents. As the examples point out, by using non-phenyl group containing, non-ionic detergents, the problem of enzymatic inhibition by SDS can be avoided.

It is preferred to use the non-phenyl group containing non-ionic detergent known as Tween 20, more precisely referred to as Poly(oxyethylene)$_n$-sorbitane-monolaurate, where "n" is usually 20. Other materials useful in accordance with the invention include Tween 20 in that it is a monooleate rather than a mono-laurate, "MEGA-10", which is N-(D-Gluco-2,3,4,5,6-pentahydroxyhexyl)-N-methyldecanamide; Deoxy-BIGCHAP, which is N, N-bis-(3-D-gluconeamidopropyl)-deoxycholamide, 1-O-n-Dodecyl-β-D-glycopyranoside, 1-O-n-Dodecyl-β-D-glucopyranosyl(1→4) α-D-glucopyranoside, 6-O-(N-heptyl-carbamoyl)-methyl-α-D-glucopyranoside, N-(D-Gluco-2,3,4,5,6-pentahydroxyhexyl)-N-methyloctanamide, 1-O-n-octyl-β-D-glucopyranoside, lauric acid sucrose ester, "Brij-35" or Dodecylpoly (oxyethyleneglycolether)$_{23}$, "Genapol X-080" or isotridecylpoly(ethylene glycol ether)$_n$, where n is 8, "Synperonic PE/F68", which is a polyethyleneco-polypropylene glycol-copolymer, "Synperonic PE/F127", which is a polyethyleneglycol-polypropylene glycol co-polymer, "Thesit", which is dodecylpoly(ethyleneglycolether)$_n$, where "n" is 9. Specifically excluded are the "Triton" detergents which include phenyl groups in their structure. This list of included and excluded detergents is far from exhaustive; however, it is assumed that the artisan is familiar with non-ionic detergents in addition to those set forth here. As with the use of the polycarboxylic acids discussed supra, once the lysis is completed, one may use the nucleic acid molecules released thereby in amplification reactions, including all of those listed above.

The artisan will note that the invention also covers, e.g., kits for use in purifying, recovering, and/or amplifying nucleic acid molecules. In their broadest embodiments, such kits include a portion of one or more lysis reagents, together with a separate portion of the materials described herein. For example, one embodiment of the invention embraces a container means, such as a box, which holds separate portions of each of a white blood cell lysis agent and polycarboxylic acids as discussed herein. A separate embodiment varies from the first in that the lysis buffer contains sodium dodecyl sulfate, and the second item in the kit is a non-phenyl group containing non-ionic detergent. These kits may also include at least one amplification reagent. For example, the kits may include a sample of *Thermus aquaticus* polymerase, or some other polymerizing enzyme. Where the kits are designed for use in a specific system, such as an HIV assay, or other similar test, separate portions of relevant primers may also be included.

Other features of the invention will be clear to the skilled artisan and need not be reiterated here.

It will be understood that the specification and examples are illustrative but not limitative of the present invention and that other embodiments within the spirit and scope of the invention will suggest themselves to those skilled in the art.

---

---

We claim:

1. Method for amplifying a nucleic acid molecule of interest, comprising (i) contacting a whole-cell-containing sample with at least one sodium dodecyl sulfate containing lysis buffer to lyse nucleic acid containing cells;

(ii) adding to said sample an amount of a water insoluble cross linked polyhydroxy polycarboxylic acid having at least two strands of formula

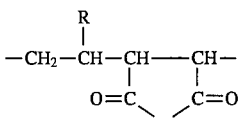

wherein one carbonyl group of at least one maleoyl moiety thereof in each strand is covalently linked to a

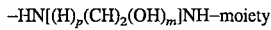

to provide the presence therein of at least one cross linking moiety of the formula:

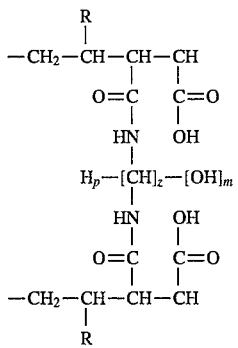

wherein R is hydrogen or lower alkylene or lower alkoxy of 1–4 carbon atoms, or phenyl, z is an integer of 1–4, p is 0 or an integer up to z-1, m is 1 or an integer up to z, wherein the ratio of cross-links to poly(alkylene carbonic acid) strands is between about 1 and about 200 to 2 sufficient to sequester any proteins in said sample;

(iii) recovering nucleic acids in said sample, wherein said recovering is accomplished without alcohol precipitation; and (iv) adding to said nucleic acids an amplification reagent which specifically amplifies said nucleic acid molecule of interest.

2. The method of claim 1, wherein said amplification reagent comprises at least one pair of primers and a nucleic acid polymerase.

3. The method of claim 3, wherein said nucleic acid is DNA.

4. The method of claim 3, wherein said DNA polymerase is a *Thermus aquaticus* derived DNA polymerase.

5. Method for amplifying a nucleic acid molecule of interest, comprising:
   (i) contacting a whole cell sample which contains said nucleic acid molecule of interest with a sodium dodecyl sulfate containing lysis buffer to form a cell lysate;
   (ii) adding to said sample an amount of a non-phenyl group containing non-ionic detergent, in an amount sufficient to inhibit enzyme inhibiting effects of sodium dodecyl sulfate; an;
   (iii) adding to said sample an amplification reagent to amplify said nucleic acid of interest; and
   (iv) amplifying said nucleic acid present in said cell lysate wherein said cell lysate contains sodium dodecyl sulfate and said non-phenyl group containing non-ionic detergent.

6. The method of claim 5, wherein said amplification reagent comprises at least two primers and a DNA polymerase.

7. The method of claim 5, wherein said non-phenyl group containing non-ionic detergent is Poly(oxyethylene)$_n$-sorbitane-monolaurate (Tween 20), where n is usually 20.

* * * * *